(12) United States Patent
Lee et al.

(10) Patent No.: US 8,494,779 B2
(45) Date of Patent: Jul. 23, 2013

(54) METHOD FOR SCREENING ESSENTIAL METABOLITES IN GROWTH OF MICROORGANISMS

(75) Inventors: Sang Yup Lee, Daejeon (KR); Hawoong Jeong, Daejeon (KR); Tae Yong Kim, Gyeonggi-do (KR); Pan-Jun Kim, Incheon (KR); Kwang Ho Lee, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 663 days.

(21) Appl. No.: 12/519,791

(22) PCT Filed: Dec. 21, 2007

(86) PCT No.: PCT/KR2007/006708
§ 371 (c)(1),
(2), (4) Date: Oct. 20, 2009

(87) PCT Pub. No.: WO2008/078911
PCT Pub. Date: Jul. 3, 2008

(65) Prior Publication Data
US 2010/0143911 A1   Jun. 10, 2010

(30) Foreign Application Priority Data
Dec. 22, 2006   (KR) .......................... 10-2006-0133119

(51) Int. Cl.
G06F 19/10 (2011.01)
G06F 19/12 (2011.01)

(52) U.S. Cl.
USPC ........................................................... 702/19

(58) Field of Classification Search
None
See application file for complete search history.

(56) References Cited

U.S. PATENT DOCUMENTS
2002/0142321 A1* 10/2002 Palsson et al. .................... 435/6
2002/0168654 A1   11/2002 Maranas et al.

FOREIGN PATENT DOCUMENTS
KR   100655495 B1   12/2006
WO   2007007933 A1   1/2007

OTHER PUBLICATIONS

Schilling et al. (Biotechnology and Bioengineering (2000/2001) vol. 71, pp. 286-306).*
Varma et al. Bio/Technology (1994) vol. 12, pp. 994-998.*
Lee, S.Y., et al., Systems biotechnology for strain improvement, Trends in Biotechnology, Jul. 2005, pp. 349-358, vol. 23, issue 7.
Papin, J.A., et al., Reconstruction of cellular signalling networks and analysis of their properties, Nature Reviews Molecular Cell Biology, Feb. 2005, pp. 99-111, vol. 6.
Datsenko, K.A., et al., One-step inactivation of chromosomal genes in *Escherichia coli* K-12 using PCR products, Proc Natl Acad Sci U.S.A., Jun. 6, 2000, pp. 6640-6645, vol. 97, No. 12.

* cited by examiner

*Primary Examiner* — Lori A Clow
(74) *Attorney, Agent, or Firm* — Tristan A. Fuierer; Andrew D. Gerschutz; Moore & Van Allen, PLLC (57) ABSTRACT

The present invention disclosed is a method for screening metabolites essential for the growth of microorganism using metabolic flux analysis. More specifically, the present invention relates to the method for screening metabolites essential for the growth of microorganism, by selecting a target microorganism, constructing a metabolic network model of the selected microorganism, inactivating the consumption reaction of each of metabolites in the constructed metabolic network model, analyzing the metabolic flux of the metabolites to select metabolites essential for the growth of the microorganism, and confirming the selected metabolites using the utilization of each of the metabolites, defined as flux sum ($\Phi$). According to the present invention, metabolites essential for the growth of microorganism, and genes involved in the essential metabolites, can be screened in a convenient manner, and drug-target genes against pathogenic microorganisms can be predicted by deleting genes associated with the metabolites screened according to the method.

14 Claims, 2 Drawing Sheets

FIG. 1

$$f = \frac{Biomass_{loss}}{Biomass_{wild}}$$

SEQUENCE LISTING

<160> NUMBER OF SEQ ID NOS: 8

<210> SEQ ID NO 1
<211> LENGTH: 72
<212> TYPE: DNA
<213> ORGANISM: Artificial Sequence
<220> FEATURE:
<223> OTHER INFORMATION: KOpurNup primer

<400> SEQUENCE: 1
atgaatattg tggtgcttat tccggcaac ggaagtaatt tacaggcaat gattgcagca    60

```
ttacacgtct tg                                                         72

<210> SEQ ID NO 2
<211> LENGTH: 71
<212> TYPE: DNA
<213> ORGANISM: Artificial Sequence
<220> FEATURE:
<223> OTHER INFORMATION: KOpurNdo primer

<400> SEQUENCE: 2
tttcgtgcat tttcagacga ccatcggcaa accagctaat caccagtgga cacttaacgg    60
ctgacatggg a                                                          71

<210> SEQ ID NO 3
<211> LENGTH: 77
<212> TYPE: DNA
<213> ORGANISM: Artificial Sequence
<220> FEATURE:
<223> OTHER INFORMATION: UPKOlpd1 primer

<400> SEQUENCE: 3
agcgctggct gaacacggta tcgtcttcgg cgaaccgaaa accgatatcg acaaggattg    60
cagcattaca cgtcttg                                                    77

<210> SEQ ID NO 4
<211> LENGTH: 71
<212> TYPE: DNA
<213> ORGANISM: Artificial Sequence
<220> FEATURE:
<223> OTHER INFORMATION: DOKOlpd1 primer

<400> SEQUENCE: 4
tcaacgcgga tgaaaccacg gtcgtcaact tccacgcctg ctttgcctgc cacttaacgg    60
ctgacatggg a                                                          71

<210> SEQ ID NO 5
<211> LENGTH: 70
<212> TYPE: DNA
<213> ORGANISM: Artificial Sequence
<220> FEATURE:
<223> OTHER INFORMATION: UPKOlpd2 primer

<400> SEQUENCE: 5
atcccttcta aagcactgct gcacgtagca aaagttatcg aagaagccaa agcgctggct    60
gaacacggta                                                            70

<210> SEQ ID NO 6
<211> LENGTH: 75
<212> TYPE: DNA
<213> ORGANISM: Artificial Sequence
<220> FEATURE:
<223> OTHER INFORMATION: DOKOlpd2 primer

<400> SEQUENCE: 6
accgacgata tcgccgatag caaagatgtg cggtacgttg gtacgcagct gtttgtcaac    60
gcggatgaaa ccacg                                                      75

<210> SEQ ID NO 7
<211> LENGTH: 70
<212> TYPE: DNA
<213> ORGANISM: Artificial Sequence
<220> FEATURE:
<223> OTHER INFORMATION: KOdlyAup primer
```

```
<400> SEQUENCE: 7
caggaaaaag tacgtcagga agagcacatc gaactgatcg cctccgaaga ttgcagcatt    60
acacgtcttg                                                            70

<210> SEQ ID NO 8
<211> LENGTH: 69
<212> TYPE: DNA
<213> ORGANISM: Artificial Sequence
<220> FEATURE:
<223> OTHER INFORMATION: KOglyAdo primer

<400> SEQUENCE: 8
ctcgataacg gcttcatcat tgatgctgtc cagcacgtca cacatccaca cttaacggct    60
gacatggga                                                             69
```

METHOD FOR SCREENING ESSENTIAL METABOLITES IN GROWTH OF MICROORGANISMS

CROSS-REFERENCE TO RELATED APPLICATIONS

This application is filed under the provisions of 35 U.S.C. §371 and claims the priority of International Patent Application No. PCT/KR2007/006708 filed on 21 Dec. 2007 entitled "Method for Screening Essential Metabolites in Growth of Microorganisms" in the name of Sang Yup LEE, et al., which claims priority of Korean Patent Application No. 10-2006-0133119 filed on 22 Dec. 2006, both of which are hereby incorporated by reference herein in their entirety.

TECHNICAL FIELD

The present invention relates to a method for screening metabolites essential for the growth of a microorganism using metabolic flux analysis, which comprises of selecting a target microorganism, constructing a metabolic network model of the selected microorganism, inactivating the consumption reaction of each of metabolites in the constructed metabolic network model, analyzing the metabolic flux of the metabolites to screen metabolites essential for the growth of the microorganism, and confirming the screened metabolites using the utilization of each of the metabolites, defined as flux sum ($\Phi$).

BACKGROUND ART

When people with weak immune system are infected with pathogenic microorganisms, the infection (all infections are not difficult to treat) will be very difficult to treat and can result in fatality. Thus, efforts to find targets for developing more effective anti-pathogenic drugs using the genomic information of pathogenic microorganisms have been actively conducted. However, it is often difficult to identify a gene candidate for drug targeting to kill pathogenic microorganisms, and it is technically difficult to determine the lethality of the relevant gene while deleting all the single genes of pathogenic microorganisms. Drug targets are mostly determined by the complex interactions between cellular components, rather than by single genes, and the deletion of a plurality of genes shows lethality, even when each gene has no lethality.

Accordingly, in order to develop effective drugs targeting pathogenic microorganisms, it is very important to understand the cellular mechanisms and interactions between microbial cellular components. Thus, the construction of metabolites and metabolic networks through the development of genomic information and functional genetics is of increasing importance in understanding the interactions between genes and proteins constituting cellular components and in constructing metabolic networks to develop effective drugs.

In fact, when new metabolic pathways, which are not found in mammalian cells, are identified in pathogenic microorganisms using metabolic network information through genomic information, it is possible to develop treatment methods targeting such metabolic characteristics to specifically attack pathogenic cells without causing side effects in human cells. If this pathogen specific metabolic pathway is identified as essential for the survival of pathogenic microorganisms, it is possible to develop a drug to inhibit the relevant metabolic pathway. It is considered that, once a drug against pathogenic microorganisms is developed, a drug for suppressing other similar pathogenic microorganisms can be easily obtained using compounds similar thereto. Analysis and prediction technology based on a metabolic network has recently become feasible with the increasing availability of genomic information. Particularly, with the development of the mathematical representation of the organisms' metabolism and its simulation using optimization techniques, it is becoming possible to predict metabolic pathway reactions occurring after deletion or addition of specific genes (Lee et al., *Trend. Biotechnol.*, 23:349, 2005). The metabolic flux analysis (MFA) technique shows the ideal metabolic flux of cells and allows for simulation and prediction of the cell behaviors, even though it does not require physiological parameters (Papin, J. et al., *Nature Reviews Molecular Cell Biology*, 6:99, 2005). Also, metabolic flux analysis is a technology of determining a change in internal metabolic flux by measuring the various coefficients of metabolic reaction equations and the production and consumption of metabolites, and is based on the assumption of a quasi-steady state.

Metabolic flux analysis is used to obtain an ideal metabolic flux space that cells can reach using only the mass balance equations and cell composition information and aims to maximize or minimize specific objective functions through a optimization method (e.g., the maximization of biomass formation or the minimization of metabolic adjustment by specific perturbation). In addition, metabolic flux analysis can be generally used to calculate the lethality of a specific gene for desired metabolites through strain improvement and to understand the metabolic pathway characteristics of strains. Also, various studies, which apply the metabolic flux analysis technique to predict metabolic flux changes occurring after the deletion or addition of genes, have been reported.

Previously, inventors developed an in-silico method for improving organisms using the flux sum of metabolites, in which the relationship of a specific metabolite with the production of useful substances can be predicted, and an organism having an increased ability to produce useful substances can be developed by introducing or amplifying genes expressing enzymes associated with specific metabolites (Korean Patent 10-655495).

US Patent Publication US2002/0168654 A1 discloses a method for in silico modeling of cellular metabolism, which can improve a flux balance analysis (FBA) model through specific constraints. In this patent publication, there was an attempt to identify the minimal set of metabolic reactions capable of supporting cellular growth, through constraints influencing the cell growth, but there was a problem in identifying synthetic lethal genes because too many combinations of mutations exist.

Thus, in the art to which the present invention pertains, there is a need to develop a method, which can precisely predict target genes in pathogenic microorganisms by examining complex microbial metabolism using a metabolic flux analysis technique in an overall viewpoint, other than using strain manipulation based on partial metabolic information, and determining the effects of manipulation of a specific gene on overall metabolic flux.

Accordingly, the present inventors have made extensive efforts to develop a method capable of efficiently predicting target genes of a pathogenic microorganism. As a result, the present inventors have found that the target genes essential for the growth of the microorganism can be screened by inactivating the consumption reaction of each metabolite in a metabolic network model, analyzing the metabolic flux of each of the metabolites, and screening for metabolites showing a decrease in cell growth rate compared to metabolites whose consumption reaction is not inactivated.

SUMMARY OF THE INVENTION

The main objective of the present invention is to provide a method for screening for metabolites essential for the growth of a microorganism using metabolic flux analysis.

Another objective of the present invention is to provide a method for screening for genes essential for the growth of a microorganism, which comprises of screening genes, which are involved in metabolites essential for the growth of a microorganism, from a metabolic network associated with the screened metabolites.

Still another objective of the present invention is to provide a method for screening substances inhibiting the growth of a pathogenic microorganism using the screened genes.

To achieve the above objectives, the present invention provides a method for screening metabolites essential for the growth of a microorganism using metabolic flux analysis, the method comprising of the steps: (a) selecting a target microorganism and constructing a metabolic network model of the selected microorganism; and (b) inactivating the consumption reaction of each of metabolites in the constructed metabolic network model, analyzing the metabolic flux of each of the metabolites, and selecting metabolites showing a greater than 50% decrease in cell growth rate, compared to the normal cell growth rate as metabolites essential for the growth of the microorganism, using Equation 2 below:

$$f = \frac{r_{loss}}{r_{wild}} \quad [\text{Equation 2}]$$

wherein $r_{wild}$ represents the normal cell growth rate, and $r_{loss}$ represents cell growth rate which decreases when the consumption reaction of the relevant metabolite is inactivated.

In the present invention, the inactivation of the consumption reaction of each of the metabolites is performed by setting the value of metabolic flux of the consumption reaction to zero (0).

The present invention provides a method for screening metabolites essential for the growth of a microorganism using metabolic flux analysis, the method may additionally comprises, after the step (b), the steps of: (c) defining the utilization of the metabolites, selected in step (b), as flux sum ($\Phi$) represented by Equation 3 below, and then calculating the flux sum ($\Phi$) of each of the metabolites; and (d) determining metabolites showing a decrease or stop in cell growth when the flux sum ($\Phi$) of each screened metabolite is reduced, confirming metabolites essential for the growth of the microorganism, as metabolites essential for the growth of the microorganism:

$$\Phi_i = \sum_{j \in P_i} S_{ij} v_j = -\sum_{j \in C_i} S_{ij} v_j = \frac{1}{2}\sum_j |S_{ij} v_j| \quad [\text{Equation 3}]$$

wherein $\Phi_i$ represents the flux sum ($\Phi$) of the $i^{th}$ metabolite, $S_{ij}$ represents the stoichiometric coefficient of the $i^{th}$ metabolite in the $j^{th}$ reaction, $v_j$ represents the metabolic flux of the $j^{th}$ reaction, $P_i$ represents a collection of metabolic reactions producing the $i^{th}$ metabolite, and $C_i$ indicates a collection of metabolic reactions consuming the $i^{th}$ metabolite.

In the present invention, the essential metabolites are selected from the group consisting of: $H^+$, $H_2O$, ATP, phosphate, ADP, nicotinamide adenine dinucleotide, nicotinamide adenine dinucleotide-reduced, $CO_2$, nicotinamide adenine dinucleotide phosphate, pyruvate, nicotinamide adenine dinucleotide phosphate-reduced, L-glutamate, coenzyme A, ammonium, AMP, acetyl-CoA, 2-oxoglutarate, acyl carrier protein, phosphoenolpyruvate, L-aspartate, L-glutamine, glyceraldehyde 3-phosphate, CMP, glycerol 3-phosphate, GTP, 5-phospho-alpha-D-ribose 1-diphosphate, dihydroxyacetone phosphate, L-alanine, L-serine, D-fructose 6-phosphate, malonyl-[acyl-carrier protein], D-glucose 1-phosphate, GDP, oxaloacetate, reduced thioredoxin, FAD, D-glucose 6-phosphate, oxidized thioredoxin, UMP, CTP, S-adenosyl-L-methionine, L-cysteine, alpha-D-ribose 5-phosphate, UDP-glucose, 5,6,7,8-tetrahydrofolate, acetoacetyl-ACP, UDP, UTP, succinyl-CoA, L-threonine, putrescine, glycine, GMP, spermidine, IMP, phosphatidylglycerol, L-arginine, L-lysine, 5,10-methylenetetrahydrofolate, chorismate, D-alanine, L-proline, L-asparagine, UDP-N-acetyl-D-glucosamine, D-glucosamine 6-phosphate, nicotinate D-ribonucleotide, dGTP, iminoaspartate, D-ribulose 5-phosphate, myristoyl-ACP (n-C14:0ACP), 3-methyl-2-oxobutanoate, L-methionine, L-tryptophan, dTMP, phosphatidate, L-valine, bicarbonate, dCTP, dUMP, L-glutamate 5-semialdehyde, meso-2,6-diaminoheptanedioate, CMP-3-deoxy-D-manno-octulosonate, undecaprenyl diphosphate, L-isoleucine, phosphatidylethanolamine, L-leucine, L-histidine, hexadecenoyl-ACP(n-C16:1ACP), 1-pyrroline-5-carboxylate, sulfite, carbamoyl phosphate, D-erythrose 4-phosphate, 3-phospho-D-glycerate, CDP-diacylglycerol, xanthosine 5'-phosphate, dTTP, L-tyrosine, L-homocysteine, dATP, 10-formyltetrahydrofolate, R-3-hydroxy-myristoyl-ACP, octadecenoyl-ACP (n-C18:1ACP), palmitoyl-ACP (n-C16:0ACP), (S)-dihydroorotate, tetradecenoyl-ACP (n-C14:1ACP), 2-oxobutanoate, 5-amino-1-(5-Phospho-D-ribosyl)imidazole-4-carboxamide, L-phenylalanine, phosphatidylserine, UDP-2,3-bis(3-hydroxytetradecanoyl)glucosamine, L-homoserine, undecaprenyl phosphate, (R)-pantothenate, orotate, L-aspartate 4-semialdehyde, sedoheptulose 7-phosphate, N2-formyl-N1-(5-phospho-D-ribosyl)glycinamide, 5-methyltetrahydrofolate, hydrogen sulfide, 7,8-dihydrofolate, dTDP, glycogen, dodecanoyl-ACP(n-C12:0ACP), 4-(1-D-ribitylamino)-5-aminouracil, prephenate, 5-amino-1-(5-phospho-D-ribosyl)imidazole, KDO(2)-lipid IV(A), N1-(5-phospho-D-ribosyl)glycinamide, 5-[(5-phospho-1-deoxyribulos-1-ylamino)methylideneamino]-1-(5-phosphoribosyl)imidazole-4-carboxamide, phosphatidylglycerophosphate, UDP-N-acetylmuramoyl-L-alanine, N-succinyl-LL-2,6-diaminoheptanedioate, 2-dehydro-3-deoxy-D-arabino-heptonate 7-phosphate, O-phospho-L-serine, UDP-N-acetylmuramate, (S)-2-[5-amino-1-(5-phospho-D-ribosypimidazole-4-carboxamido]succinate, UDP-N-acetylmuramoyl-L-alanyl-D-gamma-glutamyl-meso-2,6-diaminopimelate, 3-carboxy-3-hydroxy-4-methylpentanoate, 2,3-bis(3-hydroxytetradecanoyl)-beta-D-glucosaminyl 1-phosphate, 3-deoxy-D-manno-octulosonate 8-phosphate, N—((R)-4-phosphopantothenoyl)-L-cysteine, peptidoglycan subunit of *E. coli*, adenosine 5'-phosphosulfate, dihydropteroate, 3-dehydroshikimate, 1-(5-phosphoribosyl)-AMP, 4-methyl-2-oxopentanoate, D-glycero-D-manno-heptose 7-phosphate, 2,3,4,5-tetrahydrodipicolinate, 3-phosphohydroxypyruvate, D-glycero-D-manno-heptose 1-phosphate, D-erythro-1-(imidazol-4-yl)glycerol 3-phosphate, sulfate, UDP-3-O-(3-hydroxytetradecanoyl)-N-acetylglucosamine, 2-amino-4-hydroxy-6-(D-erythro-1,2,3-trihydroxypropyl)-7,8-dihydropteridine, UDP-3-O-(3- hydroxytetradecanoyl)-D-glucosamine, orotidine 5'-phosphate, UDP-N-acetyl-3-O-(1-carboxyvinyl)-D-glucosamine, 6-hydroxymethyl dihydropterin, O-acetyl-L-serine, UDP-N-acetylmuramoyl-L-alanyl-D-glutamyl-meso-2,6-diaminopimeloyl-D-alanyl-D-alanine, UDP-N-acetylmuramoyl-L-alanyl-D-glutamate, cardiolipin, (R)-2,3-dihydroxy-3-methylbutanoate, (S)-2-acetolactate, 3'-phosphoadenylyl sulfate, 1-(5-phosphoribosyl)-ATP, 2,3,2'3'-tetrakis(beta-hydroxymyristoyl)-D-glucosaminyl-1,6-beta-D-glucosamine 1,4'-bisphosphate, shikimate 5-phosphate, (R)-pantoate, 2-dehydropantoate, CDP-ethanolamine, 5-amino-1-(5-phospho-D-ribosyl)imidazole-4-carboxylate, 5-phospho-beta-D-ribosylamine, N-succinyl-2-L-amino-6-oxoheptanedioate, D-4'-phosphopantothenate, 3-deoxy-D-manno-2-octulosonate, ADP-L-glycero-D-manno-heptose, beta-alanine, D-alanyl-D-alanine, O-succinyl-L-homoserine, quinolinate, 2-(formamido)-N1-(5-phospho-D-ribosyl)acetamidine, D-arabinose 5-phosphate, 1-(5-phosphoribosyl)-5-[(5-phosphoribosylamino) methylideneamino] imidazole-4-carboxamide, lipopolysaccharide, 6-hydroxymethyl-dihydropterin pyrophosphate, shikimate, undecaprenyl-diphospho-N-acetylmuramoyl-L-alanyl-D-glutamyl-meso-2,6-diaminopimeloyl-D-alanyl-D-alanine, undecaprenyl-diphospho-N-acetylmuramoyl-(N-acetylglucosamine)-L-ala-D-glu-meso-2,6-diaminopimeloyl-D-ala-D-ala, 5-phosphoribosyl-5-carboxyaminoimidazole, 3-carboxy-2-hydroxy-4-methylpentanoate, N-acetyl-D-glucosamine 1-phosphate, L-cystathionine, (S)-3-methyl-2-oxopentanoate, 5-O-(1-carboxyvinyl)-3-phosphoshikimate, 2-amino-4-hydroxy-6-(erythro-1,2,3-trihydroxypropyl)dihydropteridine triphosphate, D-glycero-D-manno-heptose 1,7-bisphosphate, 3-(imidazol-4-yl)-2-oxopropyl phosphate, 3,4-dihydroxy-2-butanone 4-phosphate, KDO(2)-lipid IV(A) with laurate, 2-isopropylmaleate, KDO-lipid IV(A), ADP-D-glycero-D-manno-heptose, KDO(2)-lipid (A), N6-(1,2-dicarboxyethyl)-AMP, 5-formamido-1-(5-phospho-D-ribosyl)imidazole-4-carboxamide, lipid A disaccharide, 2,3-dihydrodipicolinate, 3-dehydroquinate, 4-phospho-L-aspartate, S-adenosylmethioninamine, 3-carboxy-4-methyl-2-oxopentanoate, phenylpyruvate, D-glucosamine 1-phosphate, dephospho-CoA, ADP-glucose, 4-aminobenzoate, L-histidinol phosphate, LL-2,6-diaminoheptanedioate, dihydroneopterin monophosphate, pantetheine 4'-phosphate, N-carbamoyl-L-aspartate, (R)-2,3-dihydroxy-3-methylpentanoate, malonyl-CoA, 4-amino-4-deoxychorismate, D-glutamate, 3-(4-hydroxyphenyl) pyruvate, L-histidinol, deamino-NAD$^+$, and (S)-2-aceto-2-hydroxybutanoate.

In the present invention, the type of the decrease in the cell growth according to the decrease in flux sum (Φ) is preferably selected from the group consisting of: a type in which the cell growth linearly decreases; a type in which the cell growth decreases below a critical value, and a type in which the cell growth decreases non-linearly, such that the cell growth stops before the flux sum (Φ) reaches zero (0). Also, the perturbation of the flux sum (Φ) preferably varies depending on the type of the decrease in the cell growth.

In another aspect, the present invention provides a method for screening genes essential for the growth of a microorganism, which comprises screening genes involved in the above-screened metabolites essential for the growth of microorganism. In the present invention, the target microorganism is *E. coli* or a pathogenic microorganism.

In still another aspect, the present invention provides a method for producing a transformed microorganism, which comprises transforming model microorganism with the above-screened genes essential for the growth of *E. coli* or a pathogenic microorganism.

In still another aspect, the present invention provides a transformed microorganism, produced according to said method, which is transformed with genes essential for the growth of *E. coli* or a pathogenic microorganism.

In yet another aspect, the present invention provides a method for screening substances inhibiting the growth of a pathogenic microorganism, the method comprising the steps of: (a) culturing said transformed microorganism in the presence of an inhibitor candidate of the growth of the pathogenic microorganism; and (b) selecting, as a substance inhibiting the growth of the pathogenic microorganism, a candidate showing the inhibition of the growth of the transformed microorganism compared to a case where the transformed microorganism is cultured in the absence of the growth inhibitor candidate.

Other features and aspects of the present invention will be apparent from the following detailed description and the appended claims.

BRIEF DESCRIPTION OF DRAWINGS

In FIG. 2, A: a case in which the cell growth rate linearly decreases as flux sum (Φ) decreases; B: a case in which the cell growth rate decreases below a critical value as flux sum (Φ) decreases, and C: a case in which the cell growth rate decreases non-linearly to reach zero (0) before the flux sum (Φ) reaches zero (0) as flux sum (Φ) decreases.

In FIG. 3, y-axis: the ratio of cell growth rate after gene deletion to normal cell growth rate; and x-axis: deleted genes (P: purN, L: lpdA, G: glyA, PL: purN/lpdA, PLG: purN/lpdA/glyA, and DX: dxs/xylB).

DETAILED DESCRIPTION OF THE INVENTION, AND PREFERRED EMBODIMENTS

As used herein, the term "perturbation" refers to a manipulation perturbing a group of all metabolites by the application of a specific external factor so as to find a metabolite having the desired property.

As used herein, the "deletion" of genes encompasses all operations of rendering specific genes inoperative in an organism, such as removing or altering all or a part of the base sequences of the genes.

As used herein, the term "culture" is defined to encompass not only the culture of microorganisms, such as bacteria, yeasts, fungi, and animal and plant cells, but also the cultivation of plants and the breeding of animals.

As used herein, the term "target microorganism" means a microorganism for screening metabolites essential for the growth thereof.

As used herein, the term "metabolic network model" means a model containing metabolic pathways, including all biochemical reactions occurring in the target microorganism.

As used herein, the term "consumption reaction of metabolites" refers to a reaction occurring in the direction in which metabolites present in a metabolic network are consumed.

1. Metabolic Network Construction

In the present invention, a new metabolic network was constructed using *E. coli* as the model strain for inhibiting the cell growth. This system comprises most of the metabolic network of *E. coli*.

2. Definition of Essential Metabolite and Screening of Essential Metabolites (1) Definition of Essential Metabolite In order to express the constructed metabolic network mathematically, a metabolic flux vector ($v_j$, the metabolic flux of $j^{th}$ metabolic reaction) can be calculated using all metabolites, their metabolic pathways and the corresponding stoichiometric matrix ($S_{ij}$; the stoichiometric coefficient of the $i^{th}$ metabolite in $j^{th}$ reaction with time). That is, a change in metabolite concentration X with time can be expressed as the sum of the fluxes of all metabolic reactions.

Also, if a change in X with time is constant, that is, in a quasi-steady state, the change in metabolite concentration X with time can be defined as the following equation 1:

$$S \cdot v = dX/dt = 0 \quad \text{[Equation 1]}$$

wherein S·v is a change in X with time, X is metabolite concentration, and t is time.

In addition, through metabolic flux analysis, the essentiality of each metabolite can be determined by examining the effect of the metabolite on the growth of cells when the cells do not consume the metabolite through a metabolic reaction. The essentiality of metabolites is determined by calculating the ratio of the growth rate of cells in a state in which all metabolic reactions consuming the respective metabolites are inactivated during the metabolic flux analysis process, to normal cell growth rate.

$$f = \frac{r_{loss}}{r_{wild}} \quad \text{[Equation 2]}$$

wherein $r_{wild}$ represents the normal growth rate of cells, and $r_{loss}$ represents cell growth rate which decreases when the consumption reaction of the relevant metabolite is inactivated.

2-2: Screening of Essential Metabolites

Figure 1:
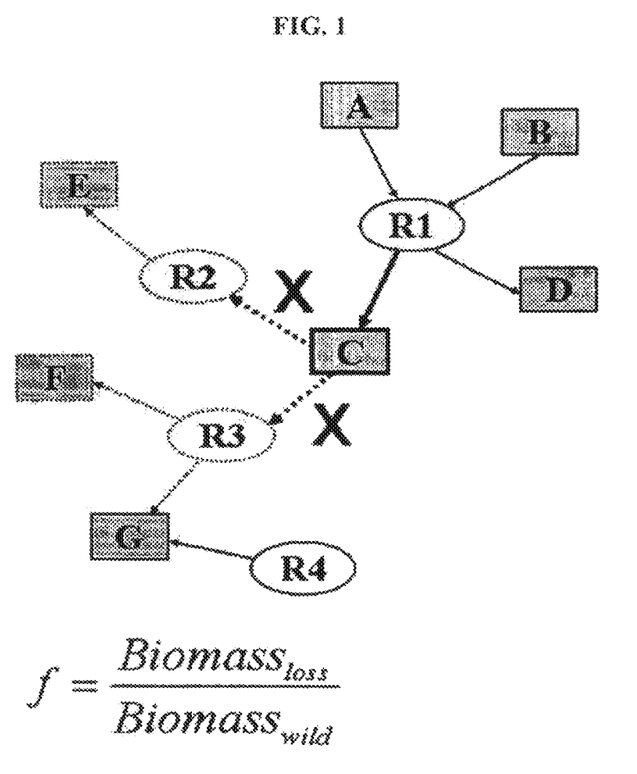
FIG. 1 is a schematic diagram for determining essential metabolites, in which, if the ratio (f) of a decrease in cell growth rate when metabolic reactions consuming the corresponding metabolite is inactivated, is smaller than 0.5, the corresponding metabolites are classified as essential metabolites, and if the ratio is greater than 0.5, the corresponding metabolites are classified as non-essential metabolites.

The reason why a metabolic reaction producing a given metabolite without consuming the metabolite is not inactivated in the analysis process for determining the essentiality of the metabolite is because, even if the metabolite is non-essential, a metabolic reaction producing the metabolite can also produce other essential metabolites, and thus, if cell growth is inhibited due to the inactivation of said metabolic reaction, originally non-essential metabolites can be wrongly understood to be essential. In view of this fact, when the calculated cell growth rate does not reach the half of normal cell growth rate, the corresponding metabolites are determined to be essential, and when the calculated cell growth rate exceeds the half, the corresponding metabolites are determined to be non-essential (FIG. 1). FIG. 1 is a schematic diagram for determining essential metabolites, in which, if the ratio (f) of a decrease in cell growth rate when metabolic reactions consuming the corresponding metabolites are inactivated, is smaller than 0.5, the corresponding metabolites are classified as essential metabolites, and if the ratio is greater than 0.5, the corresponding metabolites are classified as non-essential metabolite.

3. Definition of Flux Sum and Perturbation

In the present invention, the total amount of production or consumption of each metabolite per hour, or flux sum (Φ), was defined by Equation 3, and, when the flux sum deviated from the normal level, the effect of the corresponding metabolite on the growth of cells was systematically analyzed.

$$\Phi_i = \sum_{j \in P_i} S_{ij} v_j = -\sum_{j \in C_i} S_{ij} v_j = \frac{1}{2} \sum_j |S_{ij} v_j| \quad \text{[Equation 3]}$$

wherein $\Phi_i$ represents the flux sum (Φ) of the $i^{th}$ metabolite, $S_{ij}$ represents the stoichiometric coefficient of the $i^{th}$ metabolite in the $j^{th}$ reaction, $v_j$ represents the metabolic flux of the $j^{th}$ reaction, $P_i$ represents a set of metabolic reactions producing the $i^{th}$ metabolite, and $C_i$ represents a of metabolic reactions consuming the $i^{th}$ metabolite.

Flux sum (Φ) is an amount newly defined to express the utilization of metabolites, which has not been employed in the existing metabolic analysis method. The more the utilization of relevant metabolites is, the higher the value of Φ becomes, and the less the utilization of relevant metabolites is, the lower the value of Φ becomes.

It can be seen that, when a metabolic network is perturbed, and if the growth rate of cells does not significantly changes compared to the normal level, the flux sum (Φ) of essential metabolites also does not significantly deviate from the normal level, unlike the case of non-essential metabolites. This means that the growth rate of cells can be stabilized by maintaining the rate of production or consumption of metabolites essential for the growth of cells at a constant level. If the flux sum (Φ) of essential metabolites decreases compared to the normal level, it can lead to a decrease in the growth of cells. For example, if the flux sum (Φ) of essential metabolites decreases to half the value, the growth rate of cells will, in most cases (about 85%), decrease to half or less, and if the flux sum (Φ) of essential metabolites is reduced to a value close to zero, it can be predicted that cell growth will stop.

In prior metabolic flux analysis, the cell growth rate resulting from the deletion of a specific gene is generally determined using a method of inactivating the corresponding reaction. However, this method has a shortcoming in that, in order to examine the decrease in cell growth resulting from the deletion of more than two genes, cases associated with the combination of more than two genes must all be calculated. In contrast, in the case where the characteristics of each metabolite are examined by defining the essentiality of each metabolite and defining the utilization thereof, there is an advantage in that the decrease in cell growth resulting from the deletion of more than two genes can be easily analyzed.

EXAMPLES

Hereinafter, the present invention will be described in further detail with reference to examples. It is to be understood, however, that these examples are illustrative purpose only, and the scope of the present invention is not limited thereto.

Particularly, the following examples illustrate only a method for screening metabolites essential for the growth of microorganisms using *E. coli* as a model system, but it will be evident to those skilled in the art from the disclosure of this

Example 1

Construction of Model System

As a target strain for screening metabolites essential for the growth of microorganism, a mutant strain of *E. coli* was used to construct a new metabolic flux analysis system. This system comprises most of the metabolic network of *E. coli*. For *E. coli*, the new metabolic network consists of 979 biochemical reactions, and 814 metabolites (Lee et al., *Biotechnol. Bioproc. Eng.*, 10:425-431, 2005).

Example 2

Screening of Essential Metabolites

In the metabolic flux system constructed in Example 1, metabolic flux analysis for 814 metabolites of *E. coli* was performed. The essentiality of the metabolites is determined by calculating the ratio of the growth rate of cells in a state in which all metabolic reactions consuming the respective metabolites were inactivated, that is, in a state in which the metabolic flux of the relevant consumption reaction was set to zero (0) during the metabolic flux analysis process, to normal cell growth rate according to Equation 2.

$$f = \frac{r_{loss}}{r_{wild}} \quad \text{[Equation 2]}$$

wherein $r_{wild}$ represents the normal growth rate of cells, and $r_{loss}$ represents cell growth rate which decreases when the consumption reaction of the relevant metabolite is inactivated.

The ratio (f) of a decrease in cell growth rate when the metabolic reactions consuming the metabolites were inactivated was examined, and if the ratio was less than 0.5, the corresponding metabolites were classified as essential metabolites. Also, the essentiality of the following 814 metabolites of *E. coli* was examined under 19 cell growth conditions as described in Table 1 below: $H^+$, $H_2O$, ATP, phosphate, ADP, nicotinamide adenine dinucleotide, nicotinamide adenine dinucleotide-reduced, $CO_2$, nicotinamide adenine dinucleotide phosphate, pyruvate, nicotinamide adenine dinucleotide phosphate-reduced, L-glutamate, coenzyme A, ammonium, AMP, acetyl-CoA, 2-oxoglutarate, acyl carrier protein, phosphoenolpyruvate, L-aspartate, L-glutamine, glyceraldehyde 3-phosphate, CMP, glycerol 3-phosphate, GTP, 5-phospho-alpha-D-ribose 1-diphosphate, dihydroxyacetone phosphate, L-alanine, L-serine, D-fructose 6-phosphate, malonyl-[acyl-carrier protein], D-gucose 1-phosphate, GDP, oxaloacetate, reduced thioredoxin, FAD, D-glucose 6-phosphate, oxidized thioredoxin, UMP, CTP, S-adenosyl-L-methionine, L-cysteine, alpha-D-ribose 5-phosphate, UDP-glucose, 5,6,7,8-tetrahydrofolate, acetoacetyl-ACP, UDP, UTP, succinyl-CoA, L-threonine, putrescine, glycine, GMP, spermidine, IMP, phosphatidylglycerol, L-arginine, L-lysine, 5,10-methylenetetrahydrofolate, chorismate, D-alanine, L-proline, L-asparagine, UDP-N-acetyl-D-glucosamine, D-glucosamine 6-phosphate, nicotinate D-ribonucleotide, dGTP, iminoaspartate, D-ribulose 5-phosphate, myristoyl-ACP (n-C14:0ACP), 3-methyl-2-oxobutanoate, L-methionine, L-tryptophan, dTMP, phosphatidate, L-valine, bicarbonate, dCTP, dUMP, L-glutamate 5-semialdehyde, meso-2,6-diaminoheptanedioate, CMP-3-deoxy-D-manno-octulosonate, undecaprenyl diphosphate, L-isoleucine, phosphatidylethanolamine, L-leucine, L-histidine, hexadecenoyl-ACP(n-C16:1ACP), 1-pyrroline-5-carboxylate, sulfite, carbamoyl phosphate, D-erythrose 4-phosphate, 3-phospho-D-glycerate, CDP-diacylglycerol, xanthosine 5'-phosphate, dTTP, L-tyrosine, L-homocysteine, dATP, 10-formyltetrahydrofolate, R-3-hydroxy-myristoyl-ACP, octadecenoyl-ACP (n-C18:1ACP), palmitoyl-ACP (n-C16:0ACP), (S)-dihydroorotate, tetradecenoyl-ACP (n-C14:1ACP), 2-oxobutanoate, 5-amino-1-(5-Phospho-D-ribosyl)imidazole-4-carboxamide, L-phenylalanine, phosphatidylserine, UDP-2,3-bis(3-hydroxytetradecanoyl)glucosamine, L-homoserine, undecaprenyl phosphate, (R)-pantothenate, orotate, L-aspartate 4-semialdehyde, sedoheptulose 7-phosphate, N2-formyl-N1-(5-phospho-D-ribosyl)glycinamide, 5-methyltetrahydrofolate, hydrogen sulfide, 7,8-dihydrofolate, dTDP, glycogen, dodecanoyl-ACP(n-C12:0ACP), 4-(1-D-ribitylamino)-5-aminouracil, prephenate, 5-amino-1-(5-phospho-D-ribosyl)imidazole, KDO(2)-lipid IV(A), N1-(5-phospho-D-ribosyl)glycinamide, 5-[(5-phospho-1-deoxyribulos-1-ylamino)methylideneamino]-1-(5-phosphoribosyl)imidazole-4-carboxamide, phosphatidylglycerophosphate, UDP-N-acetylmuramoyl-L-alanine, N-succinyl-LL-2,6-diaminoheptanedioate, 2-dehydro-3-deoxy-D-arabino-heptonate 7-phosphate, O-phospho-L-serine, UDP-N-acetylmuramate, (S)-2-[5-amino-1-(5-phospho-D-ribosyl)imidazole-4-carboxamido]succinate, UDP-N-acetylmuramoyl-L-alanyl-D-gamma-glutamyl-meso-2,6-diaminopimelate, 3-carboxy-3-hydroxy-4-methyl-pentanoate, 2,3-bis(3-hydroxytetradecanoyl)-beta-D-glucosaminyl 1-phosphate, 3-deoxy-D-manno-octulosonate 8-phosphate, N—((R)-4-phosphopantothenoyl)-L-cysteine, peptidoglycan subunit of *E. coli*, adenosine 5'-phosphosulfate, dihydropteroate, 3-dehydroshikimate, 1-(5-phosphoribosyl)-AMP, 4-methyl-2-oxopentanoate, D-glycero-D-manno-heptose 7-phosphate, 2,3,4,5-tetrahydrodipicolinate, 3-phosphohydroxypyruvate, D-glycero-D-manno-heptose 1-phosphate, D-erythro-1-(imidazol-4-yl)glycerol 3-phosphate, sulfate, UDP-3-O-(3-hydroxytetradecanoyl)-N-acetylglucosamine, 2-amino-4-hydroxy-6-(D-erythro-1,2,3-trihydroxypropyl)-7,8-dihydropteridine, UDP-3-O-(3-hydroxytetradecanoyl)-D-glucosamine, orotidine 5'-phosphate, UDP-N-acetyl-3-O-(1-carboxyvinyl)-D-glucosamine, 6-hydroxymethyl dihydropterin, O-acetyl-L-serine, UDP-N-acetylmuramoyl-L-alanyl-D-glutamyl-meso-2,6-diaminopimeloyl-D-alanyl-D-alanine, UDP-N-acetylmuramoyl-L-alanyl-D-glutamate, cardiolipin, (R)-2,3-dihydroxy-3-methylbutanoate, (S)-2-acetolactate, 3'-phosphoadenyl sulfate, 1-(5-phosphoribosyl)-ATP, 2,3,2'3'-tetrakis(beta-hydroxymyristoyl)-D-glucosaminyl-1,6-beta-D-glucosamine 1,4'-bisphosphate, shikimate 5-phosphate, (R)-pantoate, 2-dehydropantoate, CDP-ethanolamine, 5-amino-1-(5-phospho-D-ribosyl)imidazole-4-carboxylate, 5-phospho-beta-D-ribosylamine, N-succinyl-2-L-amino-6-oxoheptanedioate, D-4'-phosphopantothenate, 3-deoxy-D-manno-2-octulosonate, ADP-L-glycero-D-manno-heptose, beta-alanine, D-alanyl-D-alanine, O-succinyl-L-homoserine, quinolinate, 2-(formamido)-N1-(5-phospho-D-ribosyl)acetamidine, D-arabinose 5-phosphate, 1-(5-phosphoribosyl)-5-[(5-phosphoribosylamino) methylideneamino] imidazole-4-carboxamide, lipopolysaccharide, 6-hydroxymethyl-dihydropterin pyrophosphate, shikimate, undecaprenyl-diphospho-N-acetylmuramoyl-L-alanyl-D-glutamyl-meso-2,6-diaminopimeloyl-D-alanyl-D-alanine, undecaprenyl-diphospho-N-acetylmuramoyl-(N-acetylglucosamine)-L-ala-D-glu-meso-2,6-diaminopimeloyl-D-ala-D-ala, 5-phosphoribosyl-5-carboxyaminoimidazole, 3-carboxy-2-hydroxy-4-methylpentanoate, N-acetyl-D-glucosamine 1-phosphate, L-cystathionine, (S)-3-1.0 methyl-2-oxopentanoate, 5-O-(1-carboxyvinyl)-3-phosphoshikimate, 2-amino-4-hydroxy-6-(erythro-1,2,3-trihydroxypropyl)dihydropteridine triphosphate, D-glycero-D-manno-heptose 1,7-bisphosphate, 3-(imidazol-4-yl)-2-oxopropyl phosphate, 3,4-dihydroxy-2-butanone 4-phosphate, KDO(2)-lipid IV(A) with laurate, 2-isopropylmaleate, KDO-lipid IV(A), ADP-D-glycero-D-manno-heptose, KDO(2)-lipid (A), N6-(1,2-dicarboxyethyl)-AMP, 5-formamido-1-(5-phospho-D-ribosyl)imidazole-4-carboxamide, lipid A disaccharide, 2,3-dihydrodipicolinate, 3-dehydroquinate, 4-phospho-L-aspartate, S-adenosylmethioninamine, 3-carboxy-4-methyl-2-oxopentanoate, phenylpyruvate, D-glucosamine 1-phosphate, dephospho-CoA, ADP-glucose, 4-aminobenzoate, L-histidinol phosphate, LL-2,6-diaminoheptanedioate, dihydroneopterin monophosphate, pantetheine 4'-phosphate, N-carbamoyl-L-aspartate, (R)-2,3-dihydroxy-3-methylpentanoate, malonyl-CoA, 4-amino-4-deoxychorismate, D-glutamate, 3-(4-hydroxyphenyl)pyruvate, L-histidinol, deamino-NAD$^+$, and (S)-2-aceto-2-hydroxybutanoate.

$$\Phi_i = \sum_{j \in P_i} S_{ij} v_j = -\sum_{j \in C_i} S_{ij} v_j = \frac{1}{2} \sum_j |S_{ij} v_j| \quad \text{[Equation 3]}$$

wherein $\Phi_i$ is the flux sum ($\Phi$) of the $i^{th}$ metabolite, $S_{ij}$ is the stoichiometric coefficient of the $i^{th}$ metabolite in the $j^{th}$ reaction, $v_j$ indicates the metabolic flux of the $j^{th}$ reaction, $P_i$ is a set of metabolic reactions producing the $i^{th}$ metabolite, and $C_i$ is a of metabolic reactions consuming the $i^{th}$ metabolite.

Flux sum ($\Phi$) is an amount newly defined to express the utilization of metabolites, which has not been employed in the existing metabolic analysis method. The more the utilization of relevant metabolites is, the higher the value of $\Phi$ becomes, and the less the utilization of relevant metabolites is, the lower the value of $\Phi$ becomes.

It can be seen that, when a metabolic network is perturbed, if the growth rate of cells does not significantly changes compared to the normal level, the flux sum ($\Phi$) of essential metabolites also does not significantly deviate from the nor-

TABLE 1

| No. | Culture condition | Media composition |
|---|---|---|
| 1 | glucose minimum, aerobic | glucose(10):oxygen(20) |
| 2 | glucose minimum, anaerobic | glucose(10):oxygen(0) |
| 3 | fructose minimum, aerobic | fructose(10):oxygen(20) |
| 4 | fructose minimum, anaerobic | fructose(10):oxygen(0) |
| 5 | acetate minimum, aerobic | acetate(10):oxygen(20) |
| 6 | succinate minimum, aerobic | succinate(10):oxygen(20) |
| 7 | pyruvate minimum, aerobic | pyruvate(10):oxygen(20) |
| 8 | arginine minimum, aerobic | arginine(10):oxygen(20) |
| 9 | triptophan minimum, aerobic | triptophan(10):oxygen(20) |
| 10 | glutamate minimum, aerobic | glutamate(10):oxygen(20) |
| 11 | glucose minimum, C limitation | glucose(6):oxygen(20) |
| 12 | glucose minimum, anaerobic, C limitation | glucose(6):oxygen(0) |
| 13 | glucose minimum, P limitation | glucose(10):oxygen(20):PI(0.5) |
| 14 | glucose minimum, anaerobic, P limitation | glucose(10):oxygen(0):PI(0.12) |
| 15 | glucose minimum, N limitation | glucose(10):oxygen(20):NH$_4$(5.91) |
| 16 | glucose minimum, anaerobic, N limitation | glucose(10):oxygen(0):NH$_4$(1.38) |
| 17 | glucose minimum, S limitation | glucose(10):oxygen(20):SO$_4$(0.13) |
| 18 | glucose minimum, anaerobic, S limitation | glucose(10):oxygen(0):SO$_4$(0.03) |
| 19 | glucose minimum, oxygen limitation | glucose(10):oxygen(0.6) |

As a result, it could be observed that about 87.7% of all the essential metabolites were commonly essential under the 19 growth conditions. In contrast, 12.2% of the essential metabolites were essential or non-essential depending on the 19 cell growth conditions. In addition, it was confirmed that hexadecenoyl-ACP, phosphatidylglycerol and 2-isopropylmaleate, which have not been extensively studied compared to other metabolites, were all essential for the growth of cells.

Example 3

Screening of Essential Metabolites Through Flux Sum Reduction

The flux sum of the essential metabolites screened in Example 2 was calculated, and thus the metabolites were confirmed to be essential for the growth of microorganism. That is, the total amount of hourly production or consumption (flux sum; $\Phi$) of 231 metabolites, screened in Example 2 flux sum; ($\Phi$), was defined as shown in Equation 3, and when the flux sum deviated from the normal level, its effects on the growth of cells were systematically analyzed.

mal level, unlike the case of non-essential metabolites. That is, it is considered that the growth rate of cells can be stabilized by maintaining the rate of production or consumption of metabolites essential for the growth of cells at a constant level.

If the flux sum ($\Phi$) of essential metabolites decreases compared to the normal level, it can lead to a great decrease in the growth of cells. For example, if the flux sum ($\Phi$) of essential metabolites decreases to half the value, the growth rate of cells will, in most cases (about 85%), decrease to the half or less. This is in striking contrast with the case of non-essential metabolites, only a small number (about 28.9%) of which show that effect. That is, if the flux sum ($\Phi$) of essential metabolites is reduced close to zero, the effect of stopping the growth of cells can be predicted. This change can be classified into types as shown in FIG. 2.

Figure 2:
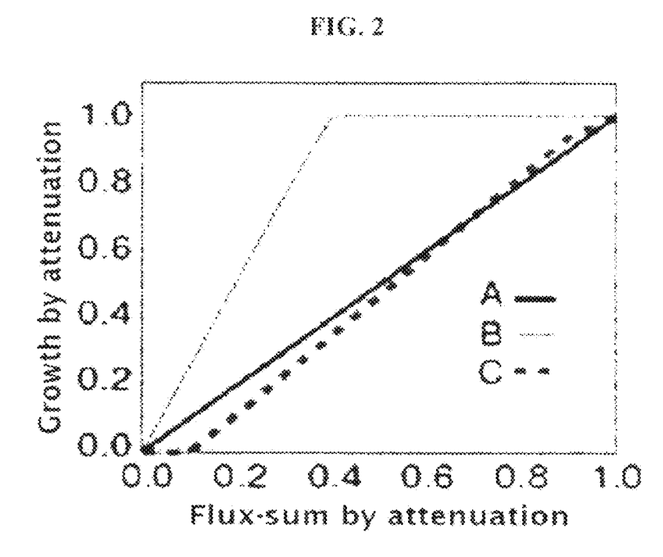
FIG. 2 shows the results of prediction of the change in cell growth rate according to the perturbation of flux sum (Φ).

In FIG. 2, the group A is the case where the growth of cells linearly decreases with a decrease in flux sum ($\Phi$), the group B is the case where the cell growth decreases below the critical value with a decrease in flux sum ($\Phi$), and the group C is the case where the cell growth decreases non-linearly with a decrease in flux sum (Φ), so that the cell growth stops before the flux sum (Φ) reaches zero.

The growth of groups A to C show a tendency to change depending on growth conditions even for the same metabolite, and the results are shown in Table 2. Table 2 shows that the decrease in flux sum (Φ) among the conditions shown in Table 1 leads to the inhibition of the growth of *E. coli*. As shown in Table 2, it can be seen that, in order to substantially inhibit the growth of cells, the perturbation of flux sum (Φ) must be changed depending on the characteristics of the groups in each of growth conditions.

TABLE 2

| Metabolite | Growth condition relevant to each type (cf. Table1) | | |
|---|---|---|---|
| | A | B | C |
| H+ | | | 1-19 |
| H2O | | | 1-19 |
| ATP | | | 1-19 |
| Phosphate | | | 1-19 |
| ADP | | | 1-19 |
| Nicotinamide adenine dinucleotide | | 1, 3, 5-7, 9-11, 13, 15, 17 | 2, 4, 8, 12, 14, 16, 18, 19 |
| Nicotinamide adenine dinucleotide - reduced | | 1, 3, 5-7, 9-11, 13, 15, 17 | 2, 4, 8, 12, 14, 16, 18, 19 |
| CO2 | 2, 4, 12, 14, 16, 18, 19 | 1, 3, 9-11, 13, 15, 17 | 5-8 |
| Nicotinamide adenine dinucleotide phosphate | 1-4, 7, 9, 11, 12, 14-19 | 5, 6, 8, 10, 13 | |
| Pyruvate | 5 | 1, 6, 8, 10, 11, 13, 15, 17 | 2-4, 7, 9, 12, 14, 16, 18, 19 |
| Nicotinamide adenine dinucleotide phosphate - reduced | 1-4, 7, 9, 11, 12, 14-19 | 5, 6, 8, 10, 13 | |
| L-Glutamate | 1-7, 9, 11, 12, 14-19 | 13 | 8, 10 |
| Coenzyme A | | 1-4, 6-19 | 5 |
| ammonium | 1-7, 11, 12, 14-19 | 10, 13 | 8, 9 |
| AMP | 2, 4-6, 8, 10, 12, 18, 19 | 1, 3, 7, 9, 11, 13-17 | |
| Acetyl-CoA | | 1-4, 6-19 | 5 |
| 2-Oxoglutarate | 2, 4, 12, 14-16, 18, 19 | 1, 3, 5-7, 9, 11, 13, 17 | 8, 10 |
| acyl carrier protein | 1, 2, 5, 7, 9, 11-19 | 3, 4, 6, 8, 10 | |
| Phosphoenolpyruvate | | 1, 5-11, 13, 15, 17 | 2-4, 12, 14, 16, 18, 19 |
| L-Aspartate | 1, 3, 11, 13, 15-17 | 2, 4-10, 12, 14, 18, 19 | |
| L-Glutamine | 1-19 | | |
| Glyceraldehyde 3-phosphate | 5, 6, 8, 10 | 7, 9 | 1-4, 11-19 |
| CMP | 1-19 | | |
| Glycerol 3-phosphate | 1-19 | | |
| GTP | 1, 3, 5, 6, 8, 10, 11, 15-18 | 2, 4, 7, 9, 12-14, 19 | |
| 5-Phospho-alpha-D-ribose 1-diphosphate | 1-15, 17-19 | 16 | |
| Dihydroxyacetone phosphate | 5-10 | 1-4, 11-19 | |
| L-Alanine | 1-19 | | |
| L-Serine | | 1-19 | |
| D-Fructose 6-phosphate | 5-10 | 1-4, 11-19 | |
| Malonyl-[acyl-carrier protein] | 1-19 | | |
| D-Glucose 1-phosphate | 1-19 | | |
| GDP | 1, 3, 5-8, 10, 11, 15-18 | 2, 4, 9, 12-14, 19 | |
| Oxaloacetate | 2, 4, 12-16 | 1, 3, 5-11, 17-19 | |
| Reduced thioredoxin | 5, 6, 8, 10, 18 | 1-4, 7, 9, 11-17, 19 | |
| FAD | 2, 4, 12-16, 18 | 1, 3, 7-11, 17, 19 | 5, 6 |
| D-Glucose 6-phosphate | 4-10 | 1, 3, 11, 13, 15, 17 | 2, 12, 14, 16, 18, 19 |
| Oxidized thioredoxin | 5, 6, 8, 10, 18 | 1-4, 7, 9, 11-17, 19 | |
| UMP | 1, 3, 5-8, 10, 11, 15, 17, 18 | 2, 4, 9, 12-14, 16, 19 | |
| CTP | 1-19 | | |
| S-Adenosyl-L-methionine | 1-19 | | |
| L-Cysteine | 1-19 | | |
| alpha-D-Ribose 5-phosphate | 5, 6, 8, 10, 18 | 1-4, 7, 9, 11-17, 19 | |
| UDP glucose | 1-19 | | |
| 5, 6, 7, 8-Tetrahydrofolate | | 1-19 | |
| Acetoacetyl-ACP | 1-19 | | |
| UDP | 1, 3, 5, 6, 8, 10, 11, 15, 17, 18 | 2, 4, 7, 9, 12-14, 16, 19 | |
| UTP | 1, 3-6, 8, 10, 11, 13-15, 17, 18 | 2, 7, 9, 12, 16, 19 | |
| Succinyl-CoA | 2, 4, 12-16, 18, 19 | 1, 3, 5-11, 17 | |
| L-Threonine | 1-12, 14-19 | 13 | |
| Putrescine | 1-7, 9-19 | 8 | |
| Glycine | 5, 6, 8, 10 | 1-4, 7, 9, 11-19 | |
| GMP | 1-19 | | |
| Spermidine | 1-19 | | |
| IMP | 1-19 | | |
| Phosphatidylglycerol | 1-19 | | |
| L-Arginine | 1-7, 9-17, 19 | 18 | 8 |
| L-Lysine | 1-19 | | |
| 5,10-Methylenetetrahydrofolate | | 1-19 | |
| Chorismate | 1-19 | | |
| D-Alanine | 1-19 | | |
| L-Proline | 1-19 | | |

TABLE 2-continued

| Metabolite | Growth condition relevant to each type (cf. Table1) | | |
|---|---|---|---|
| | A | B | C |
| L-Asparagine | 1-19 | | |
| UDP-N-acetyl-D-glucosamine | 1-19 | | |
| D-Glucosamine 6-phosphate | 1-19 | | |
| Nicotinate D-ribonucleotide | 1-19 | | |
| dGTP | 1-19 | | |
| Iminoaspartate | 1-19 | | |
| D-Ribulose 5-phosphate | 5, 6, 8, 10, 18 | 1-4, 7, 9, 11-17, 19 | |
| Myristoyl-ACP (n-C14:0ACP) | 1-19 | | |
| 3-Methyl-2-oxobutanoate | 1-12, 14-19 | 13 | |
| L-Methionine | 1-19 | | |
| L-Tryptophan | 1-8, 10-19 | | 9 |
| dTMP | 1-19 | | |
| phosphatidate | 1-19 | | |
| L-Valine | 1-19 | | |
| Bicarbonate | 1-19 | | |
| dCTP | 1-19 | | |
| dUMP | 1, 3, 5-8, 10, 11, 15, 17, 18 | 2, 4, 9, 12-14, 16, 19 | |
| L-Glutamate 5-semialdehyde | 1-19 | | |
| meso-2,6-Diaminoheptanedioate | 1-19 | | |
| CMP-3-deoxy-D-manno-octulosonate | 1-19 | | |
| Undecaprenyl diphosphate | 1-19 | | |
| L-Isoleucine | 1-12, 14-19 | 13 | |
| Phosphatidylethanolamine | 1-19 | | |
| L-Leucine | 1-12, 14-19 | 13 | |
| L-Histidine | 1-19 | | |
| Hexadecenoyl-ACP (n-C16:1ACP) | 1-19 | | |
| 1-Pyrroline-5-carboxylate | 1-19 | | |
| Sulfite | 1-19 | | |
| Carbamoyl phosphate | 1-19 | | |
| D-Erythrose 4-phosphate | | 1-19 | |
| 3-Phospho-D-glycerate | | 1, 3, 5-11, 13, 15, 17 | 2, 4, 12, 14, 16, 18, 19 |
| CDP diacylglycerol | 1-19 | | |
| Xanthosine 5'-phosphate | 1-19 | | |
| dTTP | 1-19 | | |
| L-Tyrosine | 1-19 | | |
| 1-Homocysteine | 1-19 | | |
| dATP | 2, 4-10, 12-14, 16, 18, 19 | 1, 3, 11, 15, 17 | |
| 10-Formyltetrahydrofolate | | 1-19 | |
| R-3-hydroxy-myristoyl-ACP | 1-19 | | |
| Octadecenoyl-ACP (n-C18:1ACP) | 1-19 | | |
| Palmitoyl-ACP (n-C16:0ACP) | 1-19 | | |
| (S)-Dihydroorotate | 1-19 | | |
| Tetradecenoyl-ACP (n-C14:1ACP) | 1-19 | | |
| 2-Oxobutanoate | 1-12, 14-19 | 13 | |
| 5-Amino-1-(5-Phospho-D-ribosyl)imidazole-4-carboxamide | 1-19 | | |
| L-Phenylalanine | 1-19 | | |
| phosphatidylserine | 1-19 | | |
| UDP-2,3-bis(3-hydroxytetradecanoyl)glucosamine | 1-19 | | |
| L-Homoserine | 1, 3, 11, 13, 15-17 | 2, 4-10, 12, 14, 18, 19 | |
| Undecaprenyl phosphate | 1-19 | | |
| (R)-Pantothenate | 1-19 | | |
| Orotate | 1-19 | | |
| L-Aspartate 4-semialdehyde | 1, 3, 11, 13, 15-17 | 2, 4-10, 12, 14, 18, 19 | |
| Sedoheptulose 7-phosphate | | 1-19 | |
| N2-Formyl-N1-(5-phospho-D-ribosyl)glycinamide | 1-19 | | |
| 5-Methyltetrahydrofolate | 1-19 | | |
| Hydrogen sulfide | 1-19 | | |
| 7,8-Dihydrofolate | 1-19 | | |
| dTDP | 1-19 | | |
| glycogen | 1-19 | | |
| Dodecanoyl-ACP (n-C12:0ACP) | 1-19 | | |
| 4-(1-D-Ribitylamino)-5-aminouracil | 1-19 | | |
| Prephenate | 1-19 | | |
| 5-amino-1-(5-phospho-D-ribosyl)imidazole | 1-19 | | |
| KDO(2)-lipid IV(A) | 1-19 | | |
| N1-(5-Phospho-D-ribosyl)glycinamide | 1-19 | | |
| 5-[(5-phospho-1-deoxyribulos-1-ylamino)-methylideneamino]-1-(5-phosphoribosyl)-imidazole-4-carboxamide | 1-19 | | |
| Phosphatidylglycerophosphate | 1-19 | | |
| UDP-N-acetylmuramoyl-L-alanine | 1-19 | | |
| N-Succinyl-LL-2,6-diaminoheptanedioate | 1-19 | | |
| 2-Dehydro-3-deoxy-D-arabino-heptonate 7-phosphate | 1-19 | | |
| O-Phospho-L-serine | | 1-19 | |

TABLE 2-continued

| Metabolite | A | B | C |
|---|---|---|---|
| UDP-N-acetylmuramate | 1-19 | | |
| (S)-2-[5-Amino-1-(5-phospho-D-ribosyl)imidazole-4-carboxamido]succinate | 1-19 | | |
| UDP-N-acetylmuramoyl-L-alanyl-D-gamma-glutamyl-meso-2,6-diaminopimelate | 1-19 | | |
| 3-Carboxy-3-hydroxy-4-methylpentanoate | 1-12, 14-19 | 13 | |
| 2,3-Bis(3-hydroxytetradecanoyl)-beta-D-glucosaminyl 1-phosphate | 1-19 | | |
| 3-Deoxy-D-manno-octulosonate 8-phosphate | 1-19 | | |
| N-((R)-4-Phosphopantothenoyl)-L-cysteine | 1-19 | | |
| Peptidoglycan subunit of *Escherichia coli* | 1-19 | | |
| Adenosine 5'-phosphosulfate | 1-19 | | |
| Dihydropteroate | 1-19 | | |
| 3-Dehydroshikimate | 1-19 | | |
| 1-(5-Phosphoribosyl)-AMP | 1-19 | | |
| 4-Methyl-2-oxopentanoate | 1-12, 14-19 | 13 | |
| D-Glycero-D-manno-heptose 7-phosphate | 1-19 | | |
| 2,3,4,5-Tetrahydrodipicolinate | 1-19 | | |
| 3-Phosphohydroxypyruvate | | 1-19 | |
| D-Glycero-D-manno-heptose 1-phosphate | 1-19 | | |
| D-erythro-1-(Imidazol-4-yl)glycerol 3-phosphate | 1-19 | | |
| Sulfate | 1-19 | | |
| UDP-3-O-(3-hydroxytetradecanoyl)-N-acetylglucosamine | 1-19 | | |
| 2-Amino-4-hydroxy-6-(D-erythro-1,2,3-trihydroxypropyl)-7,8-dihydropteridine | 1-19 | | |
| UDP-3-O-(3-hydroxytetradecanoyl)-D-glucosamine | 1-19 | | |
| Orotidine 5'-phosphate | 1-19 | | |
| UDP-N-acetyl-3-O-(1-carboxyvinyl)-D-glucosamine | 1-19 | | |
| 6-hydroxymethyl dihydropterin | 1-19 | | |
| O-Acetyl-L-serine | 1-19 | | |
| UDP-N-acetylmuramoyl-L-alanyl-D-glutamyl-meso-2,6-diaminopimeloyl-D-alanyl-D-alanine | 1-19 | | |
| UDP-N-acetylmuramoyl-L-alanyl-D-glutamate | 1-19 | | |
| Cardiolipin | 1-19 | | |
| (R)-2,3-Dihydroxy-3-methylbutanoate | 1-12, 14-19 | 13 | |
| (S)-2-Acetolactate | 1-12, 14-19 | 13 | |
| 3'-Phosphoadenylyl sulfate | 1-19 | | |
| 1-(5-Phosphoribosyl)-ATP | 1-19 | | |
| 2,3,2'3'-Tetrakis(beta-hydroxymyristoyl)-D-glucosaminyl-1,6-beta-D-glucosamine-1,4'-bisphosphate | 1-19 | | |
| Shikimate 5-phosphate | 1-19 | | |
| (R)-Pantoate | 1-19 | | |
| 2-Dehydropantoate | 1-19 | | |
| CDPethanolamine | 1-19 | | |
| 5-amino-1-(5-phospho-D-ribosyl)imidazole-4-carboxylate | 1-19 | | |
| 5-Phospho-beta-D-ribosylamine | 1-19 | | |
| N-Succinyl-2-L-amino-6-oxoheptanedioate | 1-19 | | |
| D-4'-Phosphopantothenate | 1-19 | | |
| 3-Deoxy-D-manno-2-octulosonate | 1-19 | | |
| ADP-L-glycero-D-manno-heptose | 1-19 | | |
| beta-Alanine | 1-19 | | |
| D-Alanyl-D-alanine | 1-19 | | |
| O-Succinyl-L-homoserine | 1-19 | | |
| Quinolinate | 1-19 | | |
| 2-(Formamido)-N1-(5-phospho-D-ribosyl)acetamidine | 1-19 | | |
| D-Arabinose 5-phosphate | 1-19 | | |
| 1-(5-Phosphoribosyl)-5-[(5-phosphoribosylamino)-methylideneamino]imidazole-4-carboxamide | 1-19 | | |
| lipopolysaccharide | 1-19 | | |
| 6-hydroxymethyl-dihydropterin pyrophosphate | 1-19 | | |
| Shikimate | 1-19 | | |
| Undecaprenyl-diphospho-N-acetylmuramoyl-L-alanyl-D-glutamyl-meso-2,6-diaminopimeloyl-D-alanyl-D-alanine | 1-19 | | |
| Undecaprenyl-diphospho-N-acetylmuramoyl-(N-acetylglucosamine)-L-ala-D-glu-meso-2,6-diaminopimeloyl-D-ala-D-ala | 1-19 | | |
| 5-phosphoribosyl-5-carboxyaminoimidazole | 1-19 | | |
| 3-Carboxy-2-hydroxy-4-methylpentanoate | 1-12, 14-19 | 13 | |
| N-Acetyl-D-glucosamine 1-phosphate | 1-19 | | |
| L-Cystathionine | 1-19 | | |
| (S)-3-Methyl-2-oxopentanoate | 1-12, 14-19 | 13 | |

TABLE 2-continued

| Metabolite | Growth condition relevant to each type (cf. Table1) | | |
|---|---|---|---|
| | A | B | C |
| 5-O-(1-Carboxyvinyl)-3-phosphoshikimate | 1-19 | | |
| 2-Amino-4-hydroxy-6-(erythro-1,2,3-trihydroxypropyl)-dihydropteridine triphosphate | 1-19 | | |
| D-Glycero-D-manno-heptose 1,7-bisphosphate | 1-19 | | |
| 3-(Imidazol-4-yl)-2-oxopropyl phosphate | 1-19 | | |
| 3,4-dihydroxy-2-butanone 4-phosphate | 1-19 | | |
| KDO(2)-lipid IV(A) with laurate | 1-19 | | |
| 2-Isopropylmaleate | 1-12, 14-19 | 13 | |
| KDO-lipid IV(A) | 1-19 | | |
| ADP-D-glycero-D-manno-heptose | 1-19 | | |
| KDO(2)-lipid (A) | 1-19 | | |
| N6-(1,2-Dicarboxyethyl)-AMP | 1-19 | | |
| 5-Formamido-1-(5-phospho-D-ribosyl)imidazole-4-carboxamide | 1-19 | | |
| Lipid A Disaccharide | 1-19 | | |
| 2,3-Dihydrodipicolinate | 1-19 | | |
| 3-Dehydroquinate | 1-19 | | |
| 4-Phospho-L-aspartate | 1, 3, 11, 13, 15-17 | 2, 4-10, 12, 14, 18, 19 | |
| S-Adenosylmethioninamine | 1-19 | | |
| 3-Carboxy-4-methyl-2-oxopentanoate | 1-12, 14-19 | 13 | |
| Phenylpyruvate | 1-19 | | |
| D-Glucosamine 1-phosphate | 1-19 | | |
| Dephospho-CoA | 1-19 | | |
| ADPglucose | 1-19 | | |
| 4-Aminobenzoate | 1-19 | | |
| L-Histidinol phosphate | 1-19 | | |
| LL-2,6-Diaminoheptanedioate | 1-19 | | |
| Dihydroneopterin monophosphate | 1-19 | | |
| Pantetheine 4'-phosphate | 1-19 | | |
| N-Carbamoyl-L-aspartate | 1-19 | | |
| (R)-2,3-Dihydroxy-3-methylpentanoate | 1-12, 14-19 | 13 | |
| Malonyl-CoA | 1-19 | | |
| 4-amino-4-deoxychorismate | 1-19 | | |
| D-Glutamate | 1-19 | | |
| 3-(4-Hydroxyphenyl)pyruvate | 1-19 | | |
| L-Histidinol | 1-19 | | |
| Deamino-NAD+ | 1-19 | | |
| (S)-2-Aceto-2-hydroxybutanoate | 1-12, 14-19 | 13 | |

In the prior metabolic flux analysis, the cell growth rate resulting from the deletion of a specific gene is generally determined using a method of inactivating the corresponding reaction. However, this method has a shortcoming in that, in order to examine the decrease in cell growth resulting from the deletion of more than two genes, cases associated with the combination of more than two genes must all be calculated. In contrast, in the case where the characteristics of each metabolite are examined by defining the essentiality of each metabolite and defining the utilization thereof, there is an advantage in that the decrease in cell growth resulting from the deletion of more than two genes can be easily analyzed.

Accordingly, the present invention provides a basis on which the amount of perturbation to be applied to each metabolite can be systematically determined by defining flux sum ($\Phi$) as the utilization of the metabolite and quantitatively evaluating the effect of a decrease in the flux sum on cell growth.

Example 4

Experimental Analysis for Cell Growth Inhibition, and Deletion of Gene Associated with Corresponding Metabolite When the flux sum ($\Phi$) of an essential metabolite was reduced to zero (0), that is, when the metabolite was not produced or consumed, the effect on cell growth was experimentally verified. Specifically, when several genes involved in the production or consumption of the essential metabolite were removed from cells, whether the growth rate of the cells changed, was examined. When each of genes is deleted, cells can continue to grow, but when the genes are deleted at the same time, the pathway producing or consuming the corresponding metabolites is blocked, which can stop the growth of cells. Tetrahydrofolate metabolites, which were essential and at the same time, classified as metabolites influencing the growth of cells when the flux sum ($\Phi$) was reduced to zero (0), were used in the experiment. It was predicted that, if genes (purN, lpdA and glyA) involved in 3 metabolic reactions among 8 metabolic reactions associated with these metabolites were deleted at the same time, the consumption of the essential tetrahydrofolate metabolites would be blocked, thus stopping the growth of cells.

In order to construct E. coli mutant strains on the basis of the above results, DNA manipulation standard protocols were used (Sambrook et al., Molecular Cloning: a Laboratory Manual, 3rd edition, 2001), and antibiotic-resistant genes in E. coli K-12 W3110 were replaced with target genes by homologous recombination through a one-step inactivation method (Warner et al., PNAS, 97(12):6640-6645, 2000) using primer sequences of Table 3, thus removing antibiotic resistance. In Table 3, $Cm^r$ indicates chloramphenicol resistance, and $Km^r$ indicates kanamycin resistance.

TABLE 3

| Template | PCR | Primer | SEQ ID NO: | Sequence (5'-3') |
|---|---|---|---|---|
| Cm' | purN | KOpurNup | 1 | ATGAATATTGTGGTGCTTATTTCCGGCAACGGAAGTAATTTACAGGCAAT GATTGCAGCATTACACGTCTTG |
|  |  | KOpurNdo | 2 | TTTCGTGCATTTTCAGACGACCATCGGCAAACCAGCTAATCACCAGTGGA CAC TTAACGGCTGACATGGGA |
| Km' | lpdA | UPKOlpd1 | 3 | AGCGCTGGCTGAACACGGTATCGTCTTCGGCGAACCGAAAACCGATATCG ACAAGGATTGCAGCATTACACGTCTTG |
|  |  | DOKOlpd1 | 4 | TCAACGCGGATGAAACCACGGTCGTCAACTTCCACGCCTGCTTTGCCTGC CACTTAACGGCTGACATGGGA |
| Km' | lpdA | UPKOlpd2 | 5 | ATCCCTTCTAAAGCACTGCTGCACGTAGCAAAAGTTATCGAAGAAGCCAA AGCGCTGGCTGAACACGGTA |
|  |  | DOKOlpd2 | 6 | ACCGACGATATCGCCGATAGCAAAGATGTGCGGTACGTTGGTACGCAGCT GTTTGTCAACGCGGATGAAACCACG |
| Cm' | glyA | KOglyAup | 7 | CAGGAAAAAGTACGTCAGGAAGAGCACATCGAACTGATCGCCTCCGAAG ATTGCAGCATTACACGTCTTG |
|  |  | KOglyAdo | 8 | CTCGATAACGGCTTCATCATTGATGCTGTCCAGCACGTCACACATCCAC ACTTAACGGCTGACATGGGA |

Figure 3:
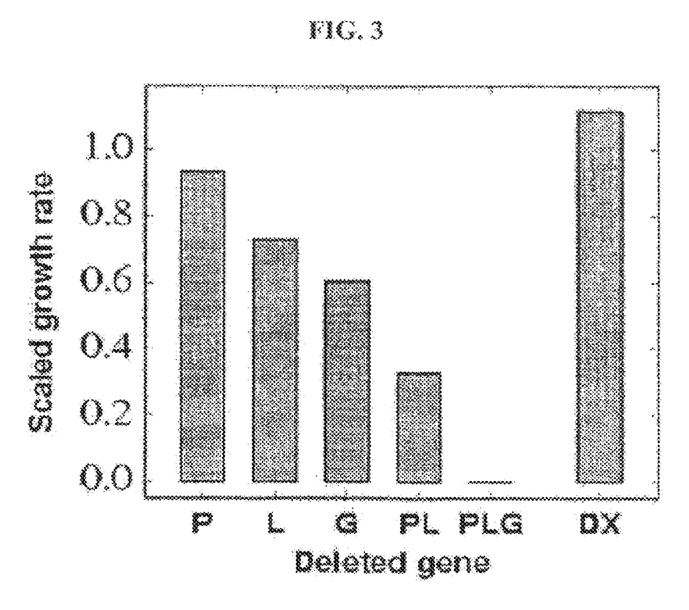
FIG. 3 shows the growth rates of cells from which essential metabolites and non-essential metabolites have been deleted.

From the above results, it could be observed that, when each of the genes was separately deleted or when two genes (purN and lpdA) were deleted at the same time, the cells continued to grow, but when all the three genes were deleted simultaneously, the growth of the cells stopped (see Table 4 and FIG. 3).

TABLE 4

| | Mutant | | | | |
|---|---|---|---|---|---|
| | Δ purN | Δ lpdA | Δ glyA | Δ purN Δ lpdA | Δ purN Δ lpdA Δ glyA |
| growth rate (μ) | 0.292 h−1 | 0.228 h−1 | 0.188 h−1 | 0.102 h−1 | no growth |

In contrast, in the case of the metabolite 1-deoxy-D-xylu-ose 5-phosphate classified as non-essential in theory, it was observed that, even when the genes (dxs and xylB) producing the metabolite were deleted, the cells did not greatly differ from the normal state (FIG. 3). In FIG. 3, P indicates the purN gene; L, the lpdA gene; G, the glyA gene; PL, the purN/lpdA genes; PLG, the purN/lpdA/glyA genes; and DX, dxs/xylB genes. Such experimental results demonstrate that the decrease in the flux sum (Φ) of essential metabolites can have a significant effect on the growth of cells, but the decrease in the flux sum (Φ) of non-essential metabolites does not have any particular effect on the growth of cells.

INDUSTRIAL APPLICABILITY

As described in detail above, according to the present invention, metabolites essential for the growth of microorganism and genes involved in the essential metabolites can be screened in a convenient manner, the growth rate of cells resulting from the decrease in the metabolic utilization (flux sum; Φ) of the essential metabolites can be predicted. Thus, drug-target genes against pathogenic microorganisms can be predicted by deleting genes associated with the metabolites screened according to the inventive method.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method for screening metabolites essential for the growth of a microorganism using metabolic flux analysis, the method comprising the steps of:
   (a) selecting a target microorganism and constructing a metabolic network model of the selected microorganism; and
   (b) inactivating a consumption reaction of each metabolite by setting a value of metabolic consumption reaction to zero in the constructed metabolic network model, analyzing a metabolic flux of each of the metabolites using a computing device processor, and selecting metabolites showing a greater than 50% decrease in cell growth rate compared to the normal growth rate, using Equation 2 below:

$$f = \frac{r_{loss}}{r_{wild}} \quad \text{[Equation 2]}$$

wherein $r_{wild}$ represents a normal cell growth rate, and $r_{loss}$ represents a cell growth rate which decreases when the consumption reaction of the relevant metabolite is inactivated;
   (c) defining utilization of the metabolites selected in step (b) as a flux sum ($\Phi$) represented by Equation 3 below, and then calculating the flux sum ($\Phi$) of each of the metabolites by using the computing device processor:

$$\Phi_i = \sum_{j \in P_i} S_{ij} v_j = -\sum_{j \in C_i} S_{ij} v_j = \frac{1}{2} \sum_j |S_{ij} v_j| \quad \text{[Equation 3]}$$

wherein $\Phi_i$ is the flux sum ($\Phi$) of an $i^{th}$ metabolite, $S_{ij}$ is a stoichiometric coefficient of the $i^{th}$ metabolite in a $i^{th}$ reaction, $v_i$ is a metabolic flux of the $i^{th}$ reaction, $P_i$ is a set of metabolic reactions producing the $i^{th}$ metabolite, and $C_i$ is a set of metabolic reactions consuming the $i^{th}$ metabolite; and
   (d) determining metabolites showing a decrease or stop in the cell growth rate when the flux sum ($\Phi$) of each metabolite is reduced as metabolites essential for the growth of the microorganism.

2. The method for screening metabolites essential for growth of a microorganism using metabolic flux analysis according to claim 1, wherein the essential metabolites are selected from the group consisting of: $H^+$, $H_2O$, ATP, phosphate, ADP, nicotinamide adenine dinucleotide, nicotinamide adenine dinucleotide-reduced, $CO_2$, nicotinamide adenine dinucleotide phosphate, pyruvate, nicotinamide adenine dinucleotide phosphate-reduced, L-glutamate, coenzyme A, ammonium, AMP, acetyl-CoA, 2-oxoglutarate, acyl carrier protein, phosphoenolpyruvate, L-aspartate, L-glutamine, glyceraldehyde 3-phosphate, CMP, glycerol 3-phosphate, GTP, 5-phospho-alpha-D-ribose 1-diphosphate, dihydroxyacetone phosphate, L-alanine, L-serine, D-fructose 6-phosphate, malonyl-[acyl-carrier protein], D-glucose 1-phosphate, GDP, oxaloacetate, reduced thioredoxin, FAD, D-glucose 6-phosphate, oxidized thioredoxin, UMP, CTP, S-adenosyl-L-methionine, L-cysteine, alpha-D-ribose 5-phosphate, UDP-glucose, 5,6,7,8-tetrahydrofolate, acetoacetyl-ACP, UDP, UTP, succinyl-CoA, L-threonine, putrescine, glycine, GMP, spermidine, IMP, phosphatidylglycerol, L-arginine, L-lysine, 5,10-methylenetetrahydrofolate, chorismate, D-alanine, L-proline, L-asparagine, UDP-N-acetyl-D-glucosamine, D-glucosamine 6-phosphate, nicotinate D-ribonucleotide, dGTP, iminoaspartate, D-ribulose 5-phosphate, myristoyl-ACP (n-C14:0 ACP), 3-methyl-2-oxobutanoate, L-methionine, L-tryptophan, dTMP, phosphatidate, L-valine, bicarbonate, dCTP, dUMP, L-glutamate 5-semialdehyde, meso-2,6-diaminoheptanedioate, CMP-3-deoxy-D-manno-octulosonate, undecaprenyl diphosphate, L-isoleucine, phosphatidylethanolamine, L-leucine, L-histidine, hexadecenoyl-ACP(n-C16:1 ACP), 1-pyrroline-5-carboxylate, sulfite, carbamoyl phosphate, D-erythrose 4-phosphate, 3-phospho-D-glycerate, CDP-diacylglycerol, xanthosine 5'-phosphate, dTTP, L-tyrosine, L-homocysteine, dATP, 10-formyltetrahydrofolate, R-3-hydroxy-myristoyl-ACP, octadecenoyl-ACP (n-C18:1ACP), palmitoyl-ACP (n-C16:0 ACP), (S)-dihydroorotate, tetradecenoyl-ACP (n-C14:1 ACP), 2-oxobutanoate, 5-amino-1-(5-Phospho-D-ribosyeimidazole-4-carboxamide, L-phenylalanine, phosphatidylserine, UDP-2,3-bis(3-hydroxytetradecanoyl)glucosamine, L-homoserine, undecaprenyl phosphate, (R)-pantothenate, orotate, L-aspartate 4-semialdehyde, sedoheptulose 7-phosphate, N2-formyl-N-1-(5-phospho-D-ribosyeglycinamide, 5-methyltetrahydrofolate, hydrogen sulfide, 7,8-dihydrofolate, dTDP, glycogen, dodecanoyl-ACP(n-C12:0 ACP), 4-(1-D-ribitylamino)-5-aminouracil, prephenate, 5-amino-1-(5-phospho-D-ribosyeimidazole, KDO(2)-lipid IV(A), N1-(5-phospho-D-ribosyeglycinamide, 5-[(5-phospho-1-deoxyribulos-1-ylamino)methylideneamino]-1-(5-phosphoribosyl)imidazole-4-carboxamide, phosphatidylglycerophosphate, UDP-N-acetylmuramoyl-L-alanine, N-succinyl-LL-2,6-diaminoheptanedioate, 2-dehydro-3-deoxy-D-arabino-heptonate 7-phosphate, O-phospho-L-serine, UDP-N-acetylmuramate, (S)-2-[5-amino-1-(5-phospho-D-ribosyeimidazole-4-carboxamido]succinate, UDP-N-acetylmuramoyl-L-alanyl-D-gamma-glutamyl-meso-2,6-diaminopimelate, 3-carboxy-3-hydroxy-4-methylpentanoate, 2,3-bis(3-hydroxytetradecanoyl)-beta-D-glucosaminyl 1-phosphate, 3-deoxy-D-manno-octulosonate 8-phosphate, N—((R)-4-phosphopantothenoyl)-L-cysteine, peptidoglycan subunit of $E.$ $coli$, adenosine 5'-phosphosulfate, dihydropteroate, 3-dehydroshikimate, 1-(5-phosphoribosyl)-AMP, 4-methyl-2-oxopentanoate, D-glycero-D-manno-heptose 7-phosphate, 2,3,4,5-tetrahydrodipicolinate, 3-phosphohydroxypyruvate, D-glycero-D-manno-heptose 1-phosphate, D-erythro-1-(imidazol-4-yl)glycerol 3-phosphate, sulfate, UDP-3-O-(3-hydroxytetradecanoyl)-N-acetylglucosamine, 2-amino-4-hydroxy-6-(D-erythro-1,2,3-trihydroxypropyl)-7,8-dihydropteridine, UDP-3-O-(3-hydroxytetradecanoyl)-D-glucosamine, orotidine 5'-phosphate, UDP-N-acetyl-3-O-(1-carboxyvinyl)-D-glucosamine, 6-hydroxymethyl dihydropterin, O-acetyl-L-serine, UDP-N-acetylmuramoyl-L-alanyl-D-glutamyl-meso-2,6-diaminopimeloyl-D-alanyl-D-alanine, UDP-N-acetylmuramoyl-L-alanyl-D-glutamate, cardiolipin, (R)-2,3-dihydroxy-3-methylbutanoate, (S)-2-acetolactate, 3'-phosphoadenylyl sulfate, 1-(5-phosphoribosyl)-ATP, 2,3, 2'3'-tetrakis(beta-hydroxymyristoyl)-D-glucosaminyl-1,6-beta-D-glucosamine 1,4'-bisphosphate, shikimate 5-phosphate, (R)-pantoate, 2-dehydropantoate, CDP-ethanolamine, 5-amino-1-(5-phospho-D-ribosyeimidazole-4-carboxylate, 5-phospho-beta-D-ribosylamine, N-succinyl-2-L-amino-6-oxoheptanedioate, D-4'-phosphopantothenate, 3-deoxy-D-manno-2-octulosonate, ADP-L-glycero-D-manno-heptose, beta-alanine, D-alanyl-D-alanine, O-succinyl-L-homoserine, quinolinate, 2-(formamido)-N1-(5-phospho-D-ribosyl)acetamidine, D-arabinose 5-phosphate, 1-(5-phosphoribosyl)-5-[(5-phosphoribosylamino)methylideneamino] imidazole-4-carboxamide, lipopolysaccharide, 6-hydroxymethyl-dihydropterin pyrophosphate, shikimate, undecaprenyl-diphospho-N-acetylmuramoyl-L-alanyl-D-glutamyl-meso-2,6-diaminopimeloyl-D-alanyl-D-alanine, undecaprenyl-diphospho-N-acetylmuramoyl-(N-acetylglucosamine)-L-ala-D-glu-meso-2,6-diaminopimeloyl-D-ala-D-ala, 5-phosphoribosyl-5-carboxyaminoimidazole, 3-carboxy-2-hydroxy-4-methylpentanoate, N-acetyl-D-glucosamine 1-phosphate, L-cystathionine, (S)-3-methyl-2-oxopentanoate, 5-O-(1-carboxyvinyl)-3-phosphoshikimate, 2-amino-4-hydroxy-6-(erythro-1,2,3-trihydroxypropyedihydropteridine triphosphate, D-glycero-D-manno-heptose 1,7-bisphosphate, 3-(imidazol-4-yl)-2-oxopropyl phosphate, 3,4-dihydroxy-2-butanone 4-phosphate, KDO(2)-lipid IV(A) with laurate, 2-isopropylmaleate, KDO-lipid IV(A), ADP-D-glycero-D-manno-heptose, KDO(2)-lipid (A), N6-(1,2-dicarboxyethyl)-AMP, 5-formamido-1-(5-phospho-D-ribosyl)imidazole-4-carboxamide, lipid A disaccharide, 2,3-dihydrodipicolinate, 3-dehydroquinate, 4-phospho-L-aspartate, S-adenosylmethioninamine, 3-carboxy-4-methyl-2-oxopentanoate, phenylpyruvate, D-glucosamine 1-phosphate, dephospho-CoA, ADP-glucose, 4-aminobenzoate, L-histidinol phosphate, LL-2,6-diaminoheptanedioate, dihydroneopterin monophosphate, pantetheine 4'-phosphate, N-carbamoyl-L-aspartate, (R)-2,3-dihydroxy-3-methylpentanoate, malonyl-CoA, 4-amino-4-deoxychorismate, D-glutamate, 3-(4-hydroxyphenyl) pyruvate, L-histidinol, deamino-NAD$^+$, and (S)-2-aceto-2-hydroxybutanoate.

3. The method for screening metabolites essential for growth of a microorganism using metabolic flux analysis according to claim 1, wherein the type of the decrease in the cell growth according to the decrease in flux sum ($\Phi$) is selected from the group consisting of: a type in which the cell growth linearly decreases; a type in which the cell growth decreases below a critical value, and a type in which the cell growth decreases non-linearly, such that the cell growth stops before the flux sum ($\Phi$) reaches zero (0).

4. The method for screening metabolites essential for growth of a microorganism using metabolic flux analysis according to claim 3, wherein the perturbation of the flux sum ($\Phi$) varies depending on the type of the decrease in the cell growth.

5. The method for screening metabolites essential for growth of a microorganism using metabolic flux analysis according to claim 1, wherein the target microorganism is $E.$ $coli$.

6. The method for screening metabolites essential for growth of a microorganism using metabolic flux analysis according to claim 1, wherein the target microorganism is a pathogenic microorganism.

7. The method for screening genes essential for growth of a microorganism, the method comprise screening genes involved in the metabolites essential for the growth of microorganism screened by the method of claim 1.

8. The method for screening genes essential for growth of a microorganism according to claim 7, wherein the microorganism is $E.$ $coli$.

9. The method for screening genes essential for growth of a microorganism according claim 7, wherein the microorganism is a pathogenic microorganism.

10. A method for producing a transformed microorganism, the method comprises transforming a model microorganism with the genes essential for the growth of the pathogenic microorganism screened by the method of claim 9.

11. A transformed microorganism produced by the method of claim 10 and transformed with genes essential for the growth of a pathogenic microorganism.

12. A method for screening substances inhibiting the growth of a pathogenic microorganism, the method comprising the steps of:
(a) culturing said transformed microorganism of claim 11 in the presence of an inhibitor candidate of the growth of the pathogenic microorganism; and
(b) selecting a candidate showing the inhibition of the growth of the transformed microorganism compared to the case where the transformed microorganism is cultured in the absence of the growth inhibitor candidate, as a substance inhibiting the growth of the pathogenic microorganism.

13. A method for producing a transformed microorganism, the method comprises transforming a model microorganism with the genes essential for the growth of $E.$ $coli$ screened by the method of claim 8.

14. A transformed microorganism produced by the method of claim 13 and transformed with genes essential for the growth of $E.$ $coli$.

* * * * *

UNITED STATES PATENT AND TRADEMARK OFFICE
CERTIFICATE OF CORRECTION

PATENT NO. : 8,494,779 B2  Page 1 of 1
APPLICATION NO. : 12/519791
DATED : July 23, 2013
INVENTOR(S) : Sang Yup Lee et al.

It is certified that error appears in the above-identified patent and that said Letters Patent is hereby corrected as shown below:

In the Claims:

Column 26, Line 56: change "ribosyeimidazole-4-carboxamide, L-phenylalanine, phos-" to --ribosyl)imidazole-4-carboxamide, L-phenylalanine, phos- --

Column 26, Line 60: change "sedoheptulose 7-phosphate, N2-formyl-N-1-(5-phospho-D-" to --sedoheptulose 7-phosphate, N2-formyl-N1-(5-phospho-D- --

Column 26, Line 61: change "ribosyeglycinamide, 5-methyltetrahydrofolate, hydrogen" to --ribosyl)glycinamide, 5-methyltetrahydrofolate, hydrogen--

Column 26, Line 64: change "prephenate, 5-amino-1-(5-phospho-D-ribosyeimidazole," to --prephenate, 5-amino-1-(5-phospho-D-ribosyl)imidazole,--

Column 26, Line 65: change "KDO(2)-lipid IV(A), N1-(5-phospho-D-ribosyeglycina-" to --KDO (2)-lipid IV(A), N1-(5-phospho-D-ribosyl)glycina- --

Column 27, Line 5: change "phospho-D-ribosyeimidazole-4-carboxamido ]succinate," to --phospho-D-ribosyl)imidazole-4-carboxamido ]succinate--

Column 27, Line 31: change "5-amino-1-(5-phospho-D-ribosyeimidazole-4-carboxylate," to --5-amino-1-(5-phospho-D-ribosyl)imidazole-4-carboxylate--

Column 27, Line 49: change "2-amino-4-hydroxy-6-(erythro-1,2,3-trihydroxypropyedihy-" to --2-amino-4-hydroxy-6-(erythro-1,2,3-trihydroxypropyl)dihy- --

Signed and Sealed this
Third Day of December, 2013

Margaret A. Focarino
*Commissioner for Patents of the United States Patent and Trademark Office*